US008965085B2

(12) United States Patent
Sakaguchi et al.

(10) Patent No.: US 8,965,085 B2
(45) Date of Patent: Feb. 24, 2015

(54) IMAGE PROCESSING APPARATUS AND X-RAY DIAGNOSIS APPARATUS

(71) Applicants: Toshiba Medical Systems Corporation, Otawara-shi (JP); Fujita Health University, Toyoake-shi (JP); The Johns Hopkins University, Baltimore, MD (US)

(72) Inventors: Takuya Sakaguchi, Utsunomiya (JP); Takashi Ichihara, Nagoya (JP); Jingwu Yao, Buffalo Grove, IL (US); Richard T. George, Baltimore, MD (US); Jeff Trost, Baltimore, MD (US); Omair Khwaja Yousuf, Baltimore, MD (US); Joao A. C. Lima, Baltimore, MD (US)

(73) Assignees: Toshiba Medical Systems Corporation, Otawara-shi (JP); Fujita Health University, Toyoake-shi (JP); The Johns Hopkins University, Baltimore, MD (US)

( * ) Notice: Subject to any disclaimer, the term of this patent is extended or adjusted under 35 U.S.C. 154(b) by 98 days.

(21) Appl. No.: 13/886,910

(22) Filed: May 3, 2013

(65) Prior Publication Data
US 2013/0243301 A1 Sep. 19, 2013

Related U.S. Application Data

(63) Continuation of application No. PCT/JP2011/075749, filed on Nov. 8, 2011.

(30) Foreign Application Priority Data

Nov. 10, 2010 (JP) .................. 2010-252092

(51) Int. Cl.
*G06K 9/00* (2006.01)
*G06T 7/00* (2006.01)
*A61B 6/00* (2006.01)

(52) U.S. Cl.
CPC ............... *G06T 7/0012* (2013.01); *A61B 6/481* (2013.01); *A61B 6/503* (2013.01); *A61B 6/5258* (2013.01); *A61B 6/504* (2013.01); *A61B 6/4441* (2013.01); *A61B 6/486* (2013.01)
USPC .......................................... 382/128; 382/132

(58) Field of Classification Search
CPC ...... A61B 6/4441; A61B 6/481; A61B 6/486; A61B 6/503; A61B 6/5258; A61B 6/504; G06T 7/0012
USPC .................................................. 382/128, 132
See application file for complete search history.

(56) References Cited

U.S. PATENT DOCUMENTS

| 4,542,459 A | 9/1985 | Riederer |
| 4,544,948 A | 10/1985 | Okazaki |

(Continued)

FOREIGN PATENT DOCUMENTS

| JP | 58-216039 | 12/1983 |
| JP | 03-141780 | 6/1991 |

(Continued)

OTHER PUBLICATIONS

International Search Report issued on Dec. 13, 2011 for PCT/JP2011/075749 filed on Nov. 8, 2011 with English Translation.

(Continued)

*Primary Examiner* — Tom Y Lu
(74) *Attorney, Agent, or Firm* — Oblon, Spivak, McClelland, Maier & Neustadt, L.L.P.

(57) ABSTRACT

An image processing apparatus according to the present embodiment includes a correcting unit. The correcting unit identifies, based on an observation value of a residual contrast material component that is injected to a subject before a predetermined timing and remains in the subject, the residual contrast material component and a new contrast material component that is newly injected to the subject after the predetermined timing regarding a contrast material component that is included in an image, and corrects an observation value of the contrast material component included in the image.

9 Claims, 10 Drawing Sheets

(56) References Cited

U.S. PATENT DOCUMENTS

| | | | |
|---|---|---|---|
| 4,716,904 A | | 1/1988 | Meno |
| 6,004,270 A | * | 12/1999 | Urbano et al. ............. 600/443 |
| 6,760,611 B1 | * | 7/2004 | Watanabe ................. 600/410 |
| 6,845,142 B2 | | 1/2005 | Ohishi |
| 7,065,395 B2 | | 6/2006 | Lienard et al. |
| 7,310,437 B2 | * | 12/2007 | Oosawa ..................... 382/132 |
| 7,496,175 B2 | | 2/2009 | Sakaguchi et al. |
| 7,949,170 B2 | | 5/2011 | Goto et al. |
| 2010/0259550 A1 | * | 10/2010 | Baumgart et al. ......... 345/589 |

FOREIGN PATENT DOCUMENTS

| | | |
|---|---|---|
| JP | 2003-000580 | 1/2003 |
| JP | 2008-073301 | 4/2008 |
| JP | 2010-246725 | 11/2010 |
| WO | 2005/046478 | 5/2005 |
| WO | 2006/051831 | 5/2006 |

OTHER PUBLICATIONS

International Written Opinion issued on Dec. 13, 2011 for PCT/JP2011/075749 filed on Nov. 8, 2011.

Yousuf et al.; "Novel Quantitative Fluoroperfusion Method Accurately Assesses the Physiologic Significance of Coronary Stenoses during Dynamic Cine Fluoroscopy"; Circulation, 122, (21 supplement), Abstract 20542, 2010.

* cited by examiner

IMAGE PROCESSING APPARATUS AND X-RAY DIAGNOSIS APPARATUS

CROSS-REFERENCE TO RELATED APPLICATIONS

This application is a continuation of PCT international application Ser. No. PCT/JP2011/075749 filed on Nov. 8, 2011 which designates the United States, and which claims the benefit of priority from Japanese Patent Application No. 2010-252092, filed on Nov. 10, 2010; the entire contents of which are incorporated herein by reference.

FIELD

Exemplary embodiments relate to an image processing apparatus and an X-ray diagnosis apparatus.

BACKGROUND

Recently, endovascular intervention treatment is becoming widespread. In the endovascular intervention treatment, a contrast material that contains iodine, for example, as a principal component is injected into blood vessels, and images are taken with an X-ray diagnosis apparatus. A doctor provides treatment while examining the images taken with the X-ray diagnosis apparatus.

During the endovascular intervention treatment, the concentration of contrast material in the body of a subject may be estimated from the images taken with the X-ray diagnosis apparatus. This is performed, for example, when the perfusion of the contrast material that flows into the tissues is to be measured to judge whether the endovascular intervention treatment can be terminated. In such a situation, the treatment is provided onto the stenosis area, and then a contrast material is newly injected to take an image. Then, the image processing apparatus or the X-ray diagnosis apparatus estimates the time change of the concentration of contrast material, based on the observation values of the contrast material components on the image.

Here, when a contrast material that contains, for example, iodine as a principal component is injected into the blood vessel, a so-called beam hardening problem occurs. For this reason, the conventional image processing apparatus or X-ray diagnosis apparatus stores therein a correction table in advance, in which the observation values of the contrast material component and the correction values of the beam hardening correction are associated with each other, corrects the observation value in accordance with a correction value that is associated with the observation value, and then estimates the concentration of contrast material in the body of the subject. To briefly explain the beam hardening problem, it is a problem that, when X-rays are applied to a contrast material that exhibits a certain concentration or higher or a certain transmission length or greater, the X-ray absorption rate becomes higher than the actual absorption rate, which makes the observation value of the contrast material component lower than the actual observation value. Due to such a nature of the problem, the correction curve indicated by the correction table does not become linear, but non-linear.

However, according to the conventional technology, the concentration of contrast material in the body of the subject may not be accurately estimated. Generally, in the endovascular intervention treatment, a contrast material is injected at several steps. The injected contrast material is eliminated through the kidney. Depending on the injected amount, however, the contrast material may be newly injected before it is completely eliminated, when the image taking of the next step may be conducted. In such a situation, the observation value on the image taken at this step may be influenced by the contrast material remaining inside the body of the subject. In the conventional technology, the correction is conducted without taking this influence into consideration, and therefore the concentration of contrast material inside the body of the subject cannot be accurately estimated.

DETAILED DESCRIPTION

An image processing apparatus according to the present embodiment includes a correcting unit. The correcting unit identifies, based on an observation value of a residual contrast material component that is injected to a subject before a predetermined timing and remains in the subject, the residual contrast material component and a new contrast material component that is newly injected to the subject after the predetermined timing regarding a contrast material component that is included in an image, and corrects an observation value of the contrast material component included in the image.

(First Embodiment)

Figure 1:
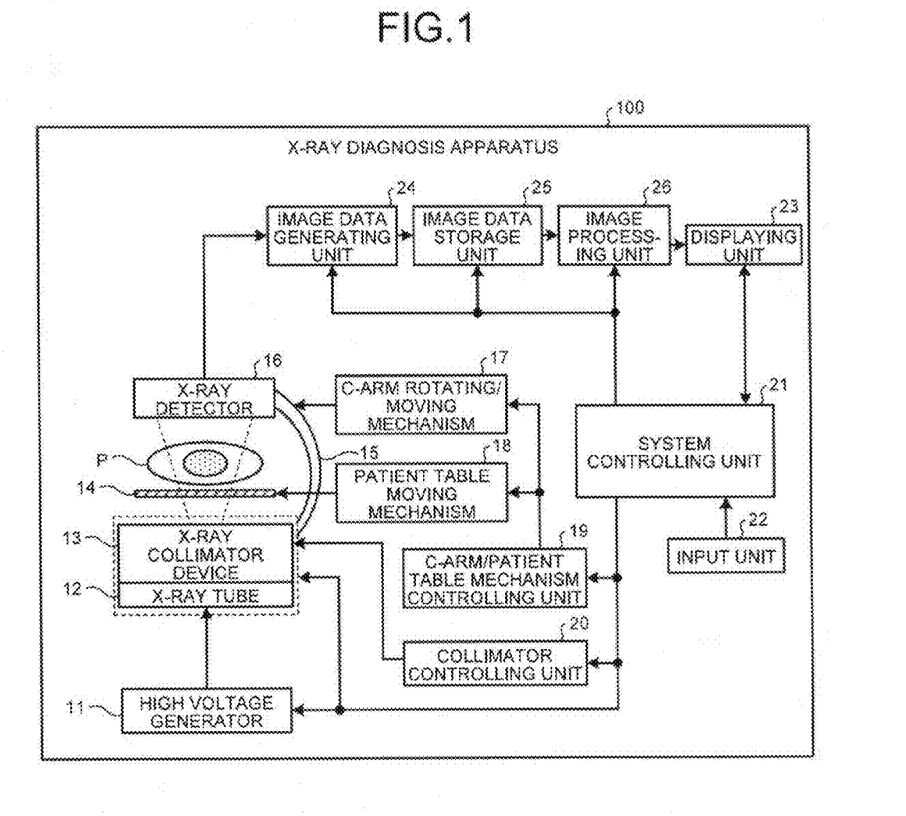
FIG. 1 is a block diagram for showing the structure of an X-ray diagnosis apparatus according to the first embodiment.

FIG. 1 is a block diagram for showing the structure of an X-ray diagnosis apparatus 100 according to the first embodiment. As illustrated in FIG. 1, the X-ray diagnosis apparatus 100 according to the first embodiment includes a high voltage generator 11, an X-ray tube 12, an X-ray collimator device 13, a patient table 14, a C-arm 15, and an X-ray detector 16. Furthermore, the X-ray diagnosis apparatus 100 according to the first embodiment includes a C-arm rotating/moving mechanism 17, a patient table moving mechanism 18, a C-arm/patient table mechanism controlling unit 19, a collimator controlling unit 20, a system controlling unit 21, an input unit 22, and a displaying unit 23. Moreover, the X-ray diagnosis apparatus 100 according to the first embodiment includes an image data generating unit 24, an image data storage unit 25, and an image processing unit 26.

Under the control of the system controlling unit 21, the high voltage generator 11 generates a high voltage, and supplies the generated high voltage to the X-ray tube 12. The X-ray tube 12 generates X-rays by use of the high voltage supplied from the high voltage generator 11.

Under the control of the collimator controlling unit 20, the X-ray collimator device 13 focuses the X-rays generated by the X-ray tube 12 in such a manner as to apply selectively to an area of interest of a subject P. For example, the X-ray collimator device 13 is provided with four slidable collimator blades. Under the control of the collimator controlling unit 20, the X-ray collimator device 13 focuses and applies the X-rays generated by the X-ray tube 12 to the subject P by sliding these collimator blades. The patient table 14 is a mattress on which the subject P lies, and is positioned on a not-shown bed. The subject P is not included in the X-ray diagnosis apparatus 100.

The X-ray detector 16 detects the X-rays that pass through the subject P. For example, the X-ray detector 16 includes detector elements arranged in a matrix form. Each detector element converts the X-rays that pass the subject P into an electrical signal and stores it, and then sends the stored electrical signal to the image data generating unit 24.

The C-arm 15 supports the X-ray tube 12, the X-ray collimator device 13, and the X-ray detector 16. The X-ray tube 12 and the X-ray collimator device 13 are arranged opposite the X-ray detector 16 with respect to the C-arm 15 so that the subject P can be positioned therebetween.

The C-arm rotating/moving mechanism 17 is a mechanism for rotating and moving the C-arm 15, and the patient table moving mechanism 18 is a mechanism for moving the patient table 14. The C-arm/patient table mechanism controlling unit 19 controls the C-arm rotating/moving mechanism 17 and the patient table moving mechanism 18 under the control of the system controlling unit 21 to adjust the rotation and movement of the C-arm 15 and the movement of the patient table 14. The collimator controlling unit 20 adjusts the aperture of the collimator blades of the X-ray collimator device 13 under the control of the system controlling unit 21, and thereby controls the application range of the X-rays that are applied to the subject P.

The image data generating unit 24 generates image data by use of the electrical signals converted from the X-rays by the X-ray detector 16, and stores the generated image data into the image data storage unit 25. For example, the image data generating unit 24 performs current-voltage conversion, analog/digital (A/D) conversion, or parallel-serial conversion onto the electrical signals received from the X-ray detector 16 to generate image data. The image data storage unit 25 stores therein the image data generated by the image data generating unit 24.

The image processing unit 26 performs various image processing onto the image data stored in the image data storage unit 25. The image processing performed by the image processing unit 26 will be discussed later.

The input unit 22 receives various instructions from a doctor or technician who operates the X-ray diagnosis apparatus 100. For example, the input unit 22 includes a mouse, a keyboard, buttons, a trackball, a joystick, and the like. The input unit 22 transfers the instructions received from the operator to the system controlling unit 21.

The displaying unit 23 displays a graphical user interface (GUI) for receiving the operator's instructions, the image data stored in the image data storage unit 25, and the like. For example, the displaying unit 23 includes a monitor. The displaying unit 23 may include more than one monitor.

The system controlling unit 21 controls the entire operation of the X-ray diagnosis apparatus 100. For example, the system controlling unit 21 controls the high voltage generator 11 in accordance with the operator's instruction transferred from the input unit 22 to adjust the voltage supplied to the X-ray tube 12, and thereby controls the application amount of X-rays applied to the subject P and the on/off. In addition, for example, the system controlling unit 21 controls the C-arm/patient table mechanism controlling unit 19 in accordance with the operator's instruction to adjust the rotation and movement of the C-arm 15 and the movement of the patient table 14. Furthermore, for example, the system controlling unit 21 controls the collimator controlling unit 20 in accordance with the operator's instruction to adjust the aperture of the collimator blades of the X-ray collimator device 13, and thereby controls the application range of X-rays that are applied to the subject P.

In addition, the system controlling unit 21 controls the image data generating process performed by the image data generating unit 24, the image processing performed by the image processing unit 26, the analysis process, and the like in accordance with the operator's instruction. Moreover, the system controlling unit 21 performs control so that the GUI for receiving instructions from the operator and images stored in the image data storage unit 25 are displayed on the monitor of the displaying unit 23.

Here, according to the first embodiment, the endovascular intervention treatment is considered. The endovascular intervention treatment includes various steps, such as steps for preparing the treatment and the step for judging the end of the treatment, in addition to the actual treatment steps (e.g. treatment for a stenosis site). Thus, in the following description, "test" is used to refer to the entire endovascular intervention treatment, while "treatment" is used to refer to the steps for conducting the actual treatment.

Figure 2:
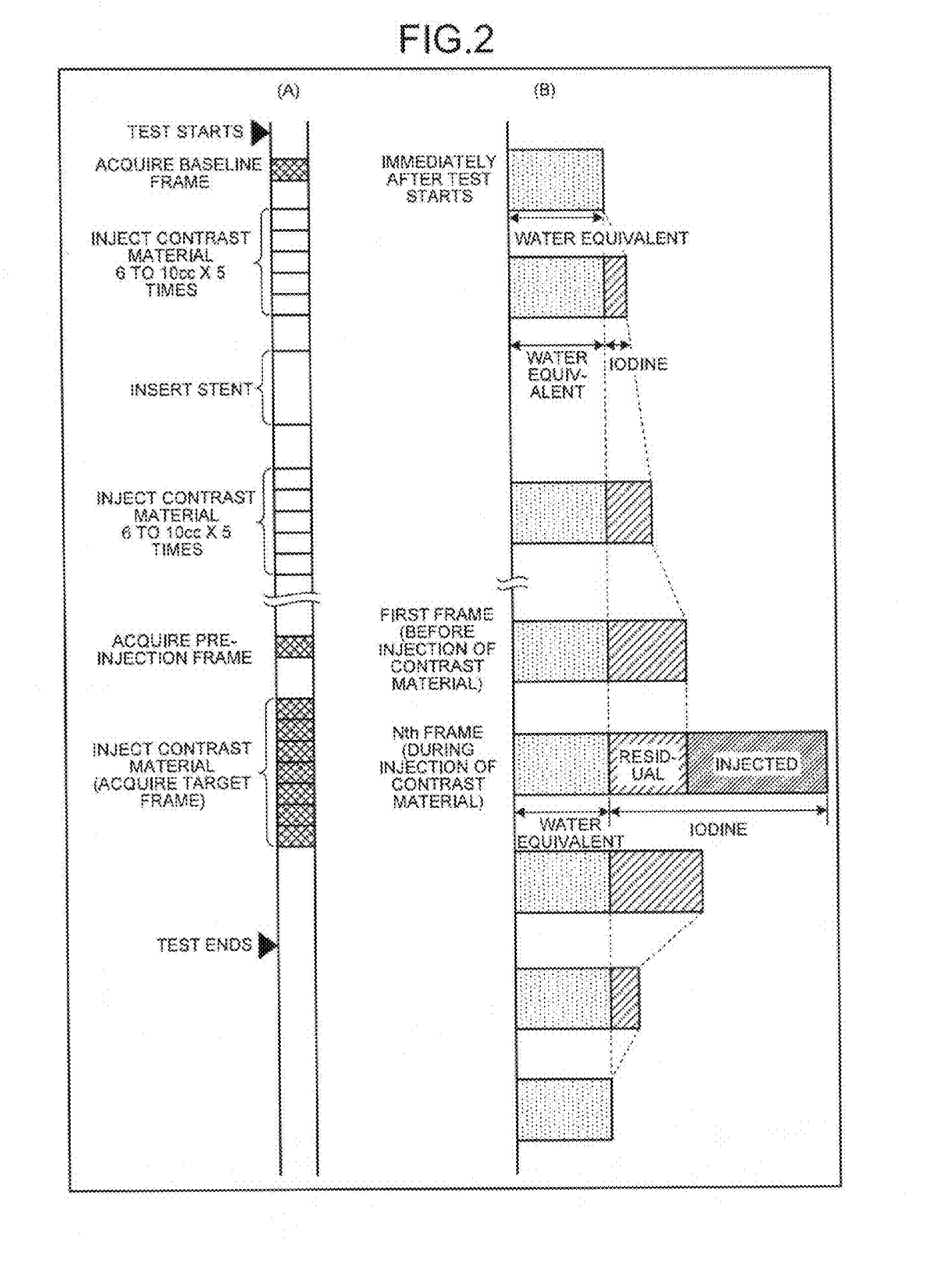
FIG. 2 is a diagram for explaining the relationship between different steps of a test and components included in an image according to the first embodiment.

FIG. 2 is a diagram for explaining the relationship between different steps included in a test and different components included in an image according to the first embodiment. In (A) of FIG. 2, different steps included in a test are shown. In (B) of FIG. 2, different components included in an image are shown.

As indicated in (A) of FIG. 2, the subject P enters the examination room, and the X-ray diagnosis apparatus 100 starts a test. According to the first embodiment, the X-ray diagnosis apparatus 100 acquires a "baseline frame" under the control of the system controlling unit 21, immediately after the test starts. Here, "immediately after the test starts" means the initial step at which the accumulation amount of contrast material injected to the subject P is a predetermined amount or less. For example, if the contrast material has not yet been injected to the subject P on the day of the test, the accumulation amount of contrast material introduced to the subject P immediately after the test starts should be "0". This means that, as indicated in (B) of FIG. 2, the only component included in the "baseline frame" is "water equivalent". Here, the component "water equivalent" corresponds to the elements of the human body (organs and bones, for example). Because their X-ray absorbance coefficients are very close to that of "water", they are referred to as "water equivalent" here. The specific value for the "predetermined amount" is preferably set to "0", but it can be arbitrarily modified in accordance with the form of the operation.

Next, as indicated in (A) of FIG. 2, preparation for the treatment is conducted. At this preparation step, the contrast material is injected into the blood vessel of the subject P five times, 6 to 10 cc for each, for example. Although the injected contrast material is eliminated through the kidney, it may not be entirely eliminated, depending on the injection amount. Thus, as indicated in (B) of FIG. 2, if an image is created at this step, the components of the image includes not only "water equivalent" but also "iodine" of the contrast material remaining in the subject P (hereinafter, "residual contrast material").

Thereafter, as indicated in (A) of FIG. 2, a stent is inserted into the blood vessel to prepare for the treatment, and then the contrast material is injected to the blood vessel of the subject P five times, 6 to 10 cc for each, for example. At this stage, the procedure may take more than one hour, and the injection amount of contrast material may exceed 100 cc. In a test for the total occlusion of the coronary artery of the heart, for example, it is not uncommon that the procedure takes more than two hours, and that the injection amount of contrast material exceeds 200 cc.

In that situation, as indicated in (B) of FIG. 2, if an image is acquired at this step, the components included in this image are not only "water equivalent" but also "iodine" of the residual contrast material, and this amount of "iodine" would gradually increase.

Thereafter, the treatment for the stenosis site is conducted (not shown), and the end of the treatment has to be judged. The end of the treatment is judged by estimating the concentration of contrast material that is newly injected. Hereinafter, this stage is referred as "estimation step", and the contrast material injected at the "estimation step" is referred to as "contrast material as an estimation target".

As indicated in (A) of FIG. 2, at the estimation step, the X-ray diagnosis apparatus 100 acquires a "pre-injection frame" under the control of the system controlling unit 21, before the contrast material as an estimation target is injected. This "pre-injection frame" is the "first frame" acquired at the estimation step. As indicated in (B) of FIG. 2, the components included in the "first frame" are "water equivalent" and "iodine" of the residual contrast material.

Moreover, at the estimation step, the X-ray diagnosis apparatus 100 acquires a "target frame" or more under the control of the system controlling unit 21 after the contrast material is injected as the estimation target, as indicated in (A) of FIG. 2. This "target frame" is the "Nth frame" of the estimation step. As indicated in (B) of FIG. 2, the components included in the "Nth frame" are "water equivalent" and "iodine", and this "iodine" includes a portion that corresponds to the residual contrast material and a portion that corresponds to the contrast material as the estimation target.

Thereafter, for example, the end of the treatment is judged, and the test ends as indicated in (A) of FIG. 2. Then, the contrast material injected to the blood vessel of the subject P is gradually eliminated through the kidney. If an image is acquired here, the component included in the image eventually becomes "water equivalent" only, as indicated in (B) of FIG. 2.

Figure 3A:
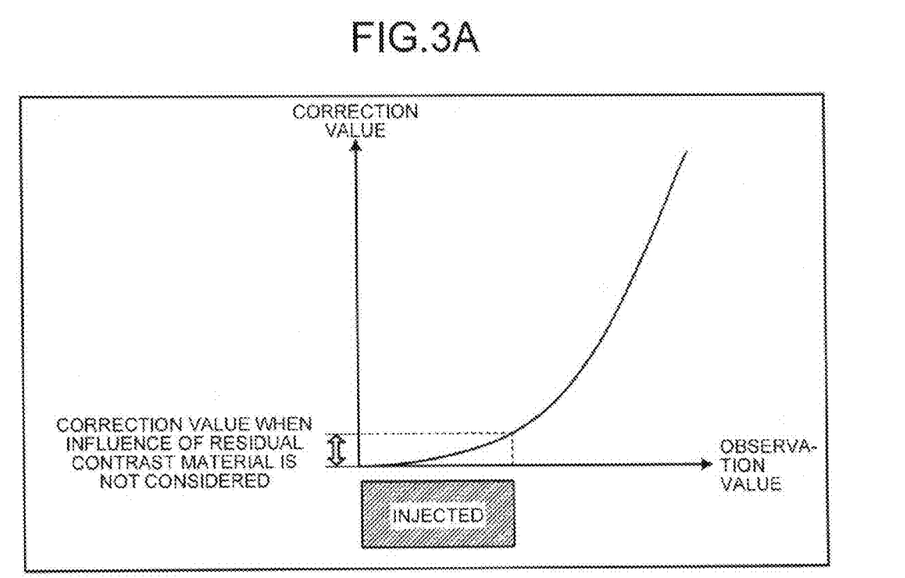
FIG. 3A is a diagram for explaining the correction value according to the first embodiment for which the influence of the residual contrast material is taken into consideration.
Figure 3B:
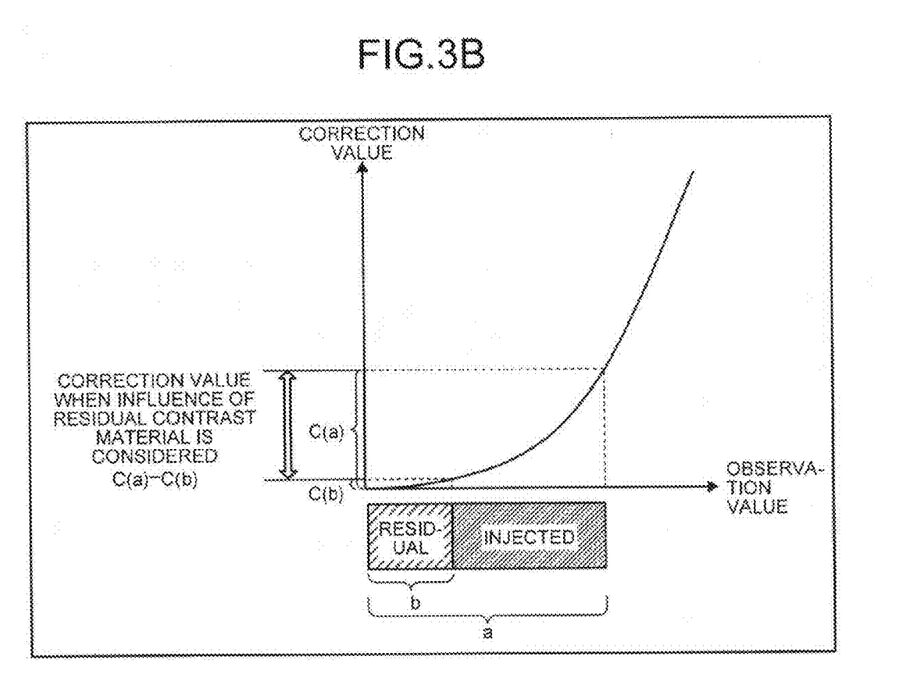
FIG. 3B is a diagram for explaining the correction value according to the first embodiment for which the influence of the residual contrast material is taken into consideration.

FIGS. 3A and 3B are diagrams for explaining the correction values determined with the influence of the residual contrast material taken into consideration according to the first embodiment. As mentioned above, the judgment regarding the end of the treatment is made by estimating the concentration of contrast material that is newly injected as the estimation target. For this reason, with a conventional technique, the observation value of the contrast material component injected as the estimation target has been calculated by subtracting the "first frame" from the "Nth frame", and the correction table is referred to by use of this value to correct the observation value based on the correction value that is associated with the observation value, as indicated in FIG. 3A.

However, as explained with reference to (B) of FIG. 2, the "Nth frame" includes "water equivalent" and "iodine", and this "iodine" component includes a portion that corresponds to the residual contrast material and a portion that corresponds to the contrast material as the estimation target. If so, the observation value obtained by subtracting the "first frame" from the "Nth frame" should be corrected, with the influence of the residual contrast material taken into consideration.

More specifically, the observation value obtained by subtracting the "first frame" from the "Nth frame" should be corrected with the correction value indicated by an open allow in FIG. 3B. In other words, although the observation values of the contrast material component injected as the estimation target do not differ between FIG. 3A and FIG. 3B, the corresponding correction values become different, depending on whether the observation value of the residual contrast material component should be offset from the point of origin because the correction curve of the correction table is non-linear. If the "first frame" is simply subtracted from the "Nth frame", the information on the observation value of the residual contrast material component would be lost, which results in insufficient correction as shown in FIG. 3A.

Figure 4:
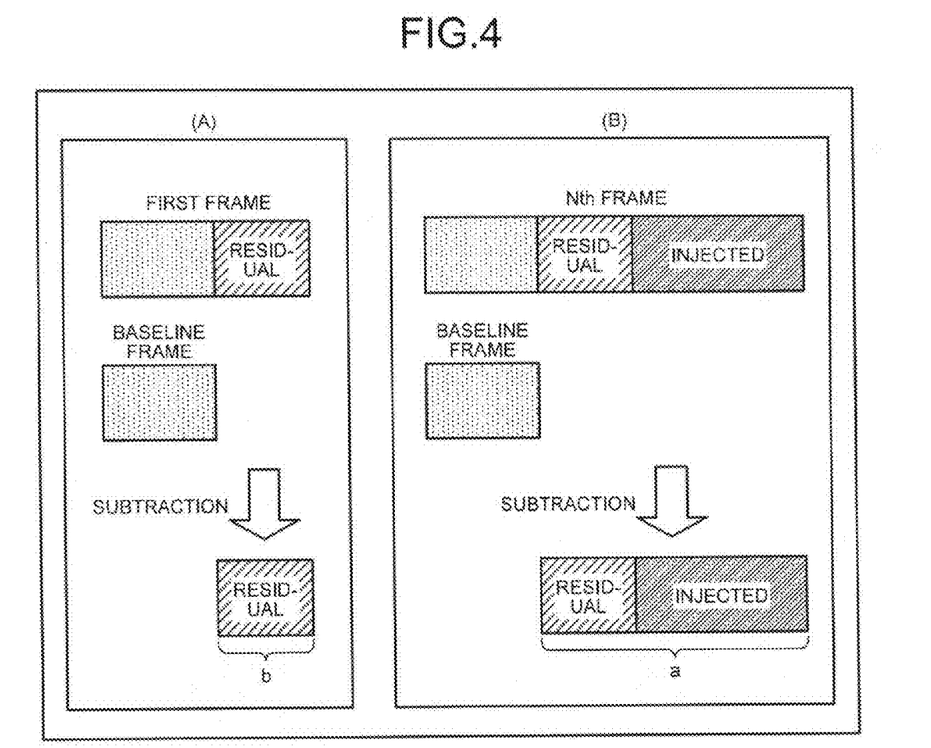
FIG. 4 is a diagram for explaining subtraction according to the first embodiment.

FIG. 4 is a diagram for explaining the subtraction according to the first embodiment. As explained with reference to FIG. 3B, the observation value obtained by subtracting the "first frame" from the "Nth frame" should be corrected by offsetting the observation value of the residual contrast material component from the point of origin. Thus, the observation value shown by the symbol a and the observation value shown by the symbol b in FIG. 3B should be calculated. Here, the symbol a denotes the total of the observation value of the residual contrast material component and the observation value of the contrast material component injected as the estimation target. Furthermore, the symbol b denotes the observation value of the residual contrast material component.

For this reason, the X-ray diagnosis apparatus 100 according to the first embodiment acquires the "baseline frame" at the initial step when the accumulation amount of contrast material injected to the subject P is a predetermined amount or less, and calculates the observation value of the symbol a and the observation value of the symbol b by use of the acquired "baseline frame".

First, the components included in the "first frame" are "water equivalent" and "iodine" of the residual contrast material. On the other hand, the component of the "baseline frame" is "water equivalent" only. Thus, as indicated in (A) of FIG. 4, the observation value obtained by subtracting the "baseline frame" from the "first frame" is the observation value of the symbol b, or in other words, the observation value of the residual contrast material component.

Furthermore, the components included in the "Nth frame" are "water equivalent" and "iodine", and this "iodine" includes a portion that corresponds to the residual contrast material and a portion that corresponds to the contrast material as the estimation target. On the other hand, the component of the "baseline frame" is "water equivalent" only. Thus, as indicated in (B) of FIG. 4, the observation value obtained by subtracting the "baseline frame" from the "Nth frame" is a total of the observation value of the symbol a, i.e., the observation value of the residual contrast material component, and the observation value of the contrast material component injected as the estimation target.

In this manner, the X-ray diagnosis apparatus 100 according to the first embodiment calculates the observation value of the symbol a and the observation value of the symbol b by use of the "baseline frame", refers to the correction table by use of the calculated observation values, and corrects the observation values based on the correction values associated with the observation values.

Figure 5:
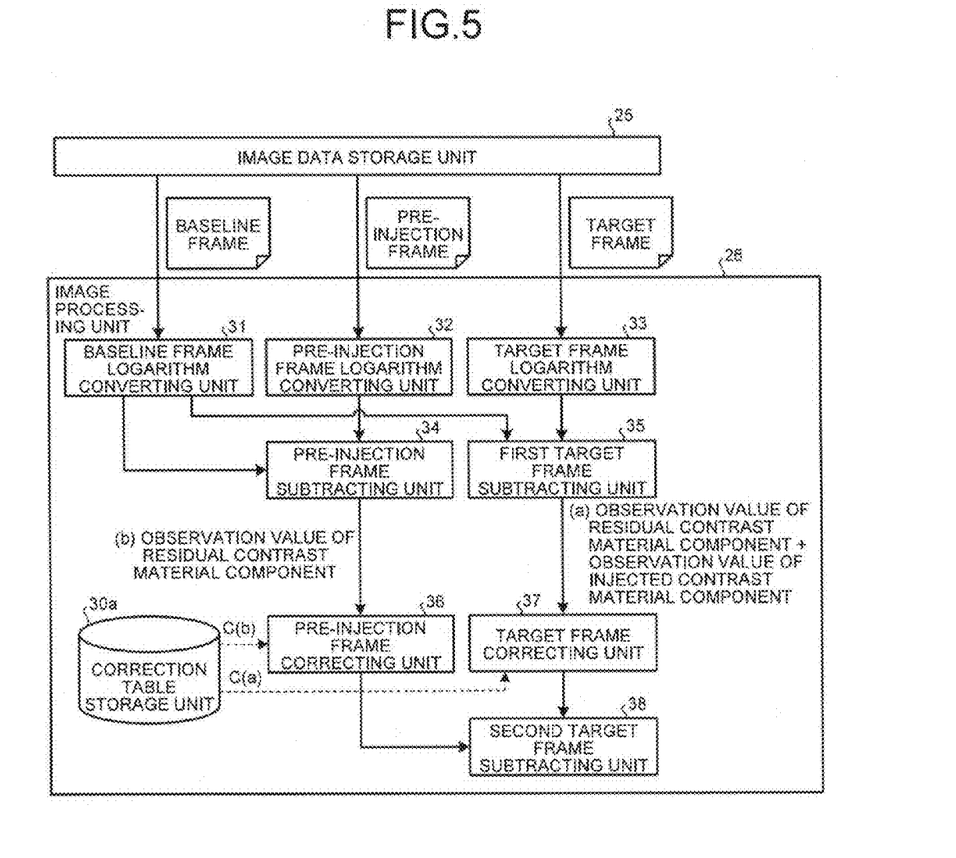
FIG. 5 is a diagram for explaining a process performed by an image processing unit according to the first embodiment.

FIG. 5 is a diagram for explaining the process performed by the image processing unit 26 according to the first embodiment. The image processing unit 26 according to the first embodiment employs the "baseline frame", the "pre-injection frame" (which corresponds to the "first frame"), and the "target frame" (which corresponds to the "Nth frame") as image processing targets.

As indicated in FIG. 5, the image processing unit 26 includes a correction table storage unit 30a. Furthermore, the image processing unit 26 includes a baseline frame logarithm converting unit 31, a pre-injection frame logarithm converting unit 32, and a target frame logarithm converting unit 33. Moreover, the image processing unit 26 includes a pre-injection frame subtracting unit 34 and a first target frame subtracting unit 35. The image processing unit 26 also includes a pre-injection frame correcting unit 36, a target frame correcting unit 37, and a second target frame subtracting unit 38.

The correction table storage unit 30a stores therein in advance a correction table in which the observation value and the correction value of the contrast material component are associated with each other. The correction curve indicated by the correction table is non-linear, as explained with reference to FIGS. 3A and 3B.

The baseline frame logarithm converting unit 31 reads the "baseline frame" from the image data storage unit 25, performs log conversion onto the read-out "baseline frame", and sends the "baseline frame" obtained from the log conversion to the pre-injection frame subtracting unit 34 and the first target frame subtracting unit 35.

The pre-injection frame logarithm converting unit 32 reads the "pre-injection frame" from the image data storage unit 25, performs log conversion onto the read-out "pre-injection frame", and sends the "pre-injection frame" obtained from the log conversion to the pre-injection frame subtracting unit 34.

The target frame logarithm converting unit 33 reads the "target frame" from the image data storage unit 25, performs log conversion onto the read-out "target frame", and sends the "target frame" obtained from the log conversion to the first target frame subtracting unit 35.

The pre-injection frame subtracting unit 34 subtracts the "baseline frame" from the "pre-injection frame" to calculate the observation value (b) of the residual contrast material component, and sends the calculated observation value (b) of the residual contrast material component to the pre-injection frame correcting unit 36.

The first target frame subtracting unit 35 subtracts the "baseline frame" from the "target frame" to calculate a total value (a) of the observation value of the residual contrast material component and the observation value of the contrast material component injected as an estimation target, and sends the calculated total value (a) to the target frame correcting unit 37.

The pre-injection frame correcting unit 36 refers to the correction table storage unit 30a by use of the observation value (b) of the residual contrast material component received from the pre-injection frame subtracting unit 34, and acquires the correction value (C(b)) that is associated with the observation value (b) of the residual contrast material component. Then, the pre-injection frame correcting unit 36 corrects the "pre-injection frame" in accordance with the acquired correction value (C(b)). As a result, the corrected "pre-injection frame" becomes an image having a value in which the beam hardening problem has been solved. Thereafter, the pre-injection frame correcting unit 36 sends the corrected "pre-injection frame" to the second target frame subtracting unit 38.

The target frame correcting unit 37 refers to the correction table storage unit 30a by use of the total value (a) received from the first target frame subtracting unit 35, and obtains the correction value (C(a)) that is associated with the total value (a). Then, the target frame correcting unit 37 corrects the "target frame" by use of the obtained correction value (C(a)). As a result, the corrected "target frame" becomes an image having a value in which the beam hardening problem has been solved. Thereafter, the target frame correcting unit 37 sends the corrected "target frame" to the second target frame subtracting unit 38.

The second target frame subtracting unit 38 subtracts the corrected "pre-injection frame" received from the pre-injection frame correcting unit 36, from the corrected "target frame" received from the target frame correcting unit 37, and calculates the observation value of the contrast material component injected as the estimation target. Because the corrected "target frame" and the corrected "pre-injection frame" are images each having a value in which the beam hardening problem has been solved, the second target frame subtracting unit 38 does not have to conduct additional corrections onto the calculated value of the contrast material component to deal with the beam hardening problem.

Figure 6:
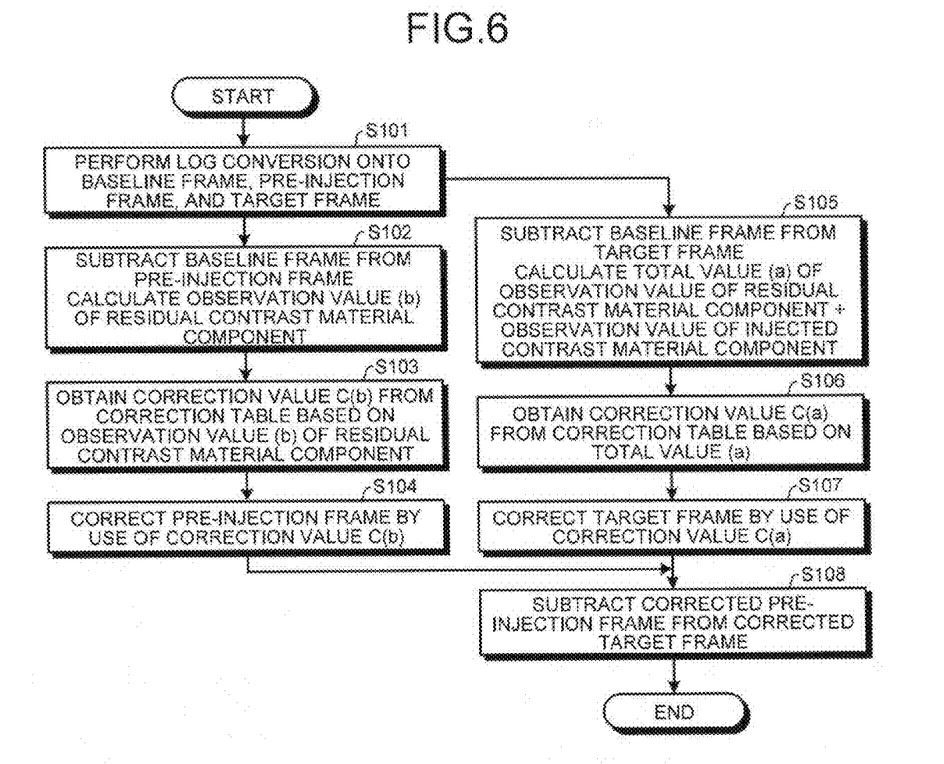
FIG. 6 is a flowchart of the procedure of the process performed by the image processing unit according to the first embodiment.

FIG. 6 is a flowchart of the procedure of the process performed by the image processing unit 26 according to the first embodiment. As indicated in FIG. 6, first, the image processing unit 26 performs log conversion onto the "baseline frame", the "pre-injection frame", and the "target frame" (step S101). More specifically, the baseline frame logarithm converting unit 31 performs log conversion onto the "baseline frame", the pre-injection frame logarithm converting unit 32 performs log conversion onto the "pre-injection frame", and the target frame logarithm converting unit 33 performs log conversion onto the "target frame".

Next, the image processing unit 26 subtracts the log-converted "baseline frame" from the log-converted "pre-injection frame", and thereby calculates the observation value (b) of the residual contrast material component (step S102). More specifically, the pre-injection frame subtracting unit 34 calculates the observation value (b) of the residual contrast material component.

Thereafter, the image processing unit 26 refers to the correction table storage unit 30a by use of the calculated observation value (b) of the residual contrast material component, and acquires the correction value (C(b)) that is associated with the observation value (b) of the residual contrast material component (step S103). More specifically, the pre-injection frame correcting unit 36 acquires the correction value (C(b)).

Then, the image processing unit 26 corrects the "pre-injection frame" by use of the acquired correction value (C(b)) (step S104). More specifically, the pre-injection frame correcting unit 36 corrects "pre-injection frame".

On the other hand, the image processing unit 26 subtracts the log-converted "baseline frame" from the log-converted "target frame" after the log conversion at step S101, and calculates the total value (a) of the observation value of the residual contrast material component and the observation value of the contrast material component injected as the estimation target (step S105). More specifically, the first target frame subtracting unit 35 calculates the total value (a).

Thereafter, the image processing unit 26 refers to the correction table storage unit 30a by use of the calculated total value (a), and acquires the correction value (C(a)) that is associated with the total value (a) (step S106). More specifically, the target frame correcting unit 37 acquires the correction value (C(a)).

Then, the image processing unit 26 corrects the "target frame" by use of the acquired correction value (C(a)) (step S107). More specifically, the target frame correcting unit 37 corrects the "target frame".

Thereafter, the image processing unit 26 subtracts the corrected "pre-injection frame" from the corrected "target frame", and calculates the observation value of the contrast material component injected as the estimation target (step S108). More specifically, the second target frame subtracting unit 38 calculates the observation value of the contrast material component injected as the estimation target.

The procedure of the process performed by the image processing unit 26 according to the first embodiment is not limited to the process procedure indicated in FIG. 6. For example, the image processing unit 26 may execute the process of steps S102 through S104 and the process of steps S105 through S107 in parallel. Furthermore, for example, the image processing unit 26 may execute part of the image processing including the log conversion beforehand, which can be executed with the "baseline frame" and the "pre-injection frame" only, and then execute the rest of the image processing after the "target frame" is acquired. If the "target frame" includes multiple frames that are sequentially collected, the image processing unit 26 may execute the image processing after all the "target frames" are collected, or sequentially execute the image processing each time they are collected. As explained above, the process procedure of the image processing unit 26 can be suitably changed.

As shown above, the X-ray diagnosis apparatus 100 according to the first embodiment, based on the observation value of the residual contrast material component included in the "target frame", corrects the observation value of the contrast material component that serves as the estimation target of the concentration of contrast material, out of the contrast material components included in this "target frame". As a result, the concentration of contrast material in a subject according to the first embodiment can be accurately estimated. For example, an accurate time curve for the concentration of contrast material from which the influence of the residual contrast material is eliminated can be attained, and the perfusion analysis can be accurately conducted.

Furthermore, according to the first embodiment, as in the endovascular intervention treatment that employs different contrast material for different cases, without worrying about the amount of residual contrast material component, the concentration of contrast material in the subject can be accurately estimated.

In addition, according to the first embodiment, the pre-injection frame subtracting unit 34 subtracts the "baseline frame" from the "pre-injection frame", and calculates the observation value of the residual contrast material component included in the "target frame". Moreover, the first target frame subtracting unit 35 subtracts the "baseline frame" from the "target frame" and the total of the observation value of the residual contrast material component and the observation value of the contrast material component injected as the estimation target. Then, based on the correction value that is associated with the observation value of the residual contrast material component and the correction value that is associated with the total value, the pre-injection frame correcting unit 36, the target frame correcting unit 37, and the second target frame subtracting unit 38 corrects the observation value of the contrast material component that serves as the estimation target of the concentration of contrast material, among the contrast material components included in the "target frame".

As discussed above, according to the first embodiment, the observation value of the residual contrast material component can be calculated, and the subtraction can be performed after accurately correcting the "pre-injection frame" and the "target frame", the observation value of the contrast material component as the estimation target can be accurately obtained.

(Second Embodiment)

Next, the X-ray diagnosis apparatus 100 according to the second embodiment is explained. The X-ray diagnosis apparatus 100 according to the second embodiment brings the condition for acquiring the "baseline frame" into agreement with the condition for acquiring the "pre-injection frame" and the "target frame".

Figure 7:
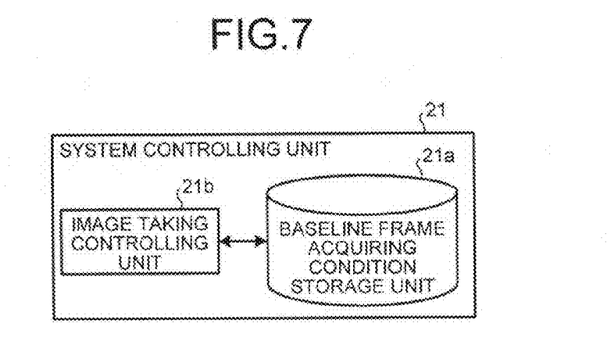
FIG. 7 is a diagram for explaining a system controlling unit according to the second embodiment.

FIG. 7 is a diagram for explaining the system controlling unit 21 according to the second embodiment. As indicated in FIG. 7, the system controlling unit 21 according to the second embodiment includes a baseline frame acquiring condition storage unit 21a. The baseline frame acquiring condition storage unit 21a stores therein acquiring conditions for acquiring the "baseline frame". Here, the acquiring conditions are, for example, the voltage supplied to the X-ray tube 12, the rotation angle of the C-arm 15, the position of the patient table 14, the X-ray irradiation range, the cardiac phase of the subject P, the respiratory phase, and the like.

An image taking controlling unit 21b of the system controlling unit 21 controls the high voltage generator 11, the C-arm/patient table mechanism controlling unit 19, and the collimator controlling unit 20 when the "baseline frame" is acquired, and stores various acquiring conditions that are mentioned above into the baseline frame acquiring condition storage unit 21a. Furthermore, the image taking controlling unit 21b of the system controlling unit 21 reads the acquiring conditions from the baseline frame acquiring condition storage unit 21a when acquiring the "pre-injection frame" and the "target frame". Then, the image taking controlling unit 21b controls the high voltage generator 11, the C-arm/patient table mechanism controlling unit 19, the collimator controlling unit 20, and the like to take an image in such a manner as to suit the read-out acquiring conditions.

Thus, according to the second embodiment, the conditions for acquiring the "baseline frame" are brought into agreement with the conditions for acquiring the "pre-injection frame" and the "target frame", and therefore the accuracy of the subtraction can be improved.

(Third Embodiment)

Next, the X-ray diagnosis apparatus 100 according to the third embodiment is explained. The X-ray diagnosis apparatus 100 according to the third embodiment when performing the subtraction performs position adjustment among images.

As explained with reference to FIG. 2, the "baseline frame" is acquired, for example, immediately after the test is started, but the "pre-injection frame" and the "target frame" are acquired, for example, one hour after the "baseline frame" is acquired. The subject P may move in the meantime, which may lower the precision of the subtraction.

For this reason, the X-ray diagnosis apparatus 100 according to the third embodiment performs position adjustment among the images. More specifically, a pre-injection frame subtracting unit 34 first adjusts the positions of the "baseline frame" and the "pre-injection frame" before subtracting the "baseline frame" from the "pre-injection frame". Moreover, the first target frame subtracting unit 35 first adjusts the positions of the "baseline frame" and the "target frame" before subtracting the "baseline frame" from the "target frame".

The positional adjustment of the images can be realized with the publicly known technique. For example, the pre-injection frame subtracting unit 34 and the first target frame subtracting unit 35 uses image data of one image as a reference and moves image data of the other pixel by pixel, and thereby obtains the amount of movement that maximizes the similarity between the image data. Then, the pre-injection frame subtracting unit 34 and the first target frame subtracting unit 35 corrects the other image data based on the obtained amount of movement.

In this manner, according to the third embodiment, the accuracy of subtraction can be further improved. The method of adjusting the positions of the images according to the third embodiment is effective whether or not the X-ray diagnosis apparatus 100 combines electrocardiogram (ECG) gating or respiratory gating in image taking. If the imaging target is, for example, the heart, the X-ray diagnosis apparatus 100 often uses ECG gating or respiratory gating in combination for image taking. In contrast, if the imaging target is an organ that does not move, the X-ray diagnosis apparatus 100 does not use ECG gating or respiratory gating in combination for image taking. In either situation, the position of the "baseline frame" tends to be shifted from the positions of the "pre-injection frame" and the "target frame", and thus the method according to the third embodiment is effective. The positional adjustment of the images may be combined with the first embodiment or with the second embodiment.

(Fourth Embodiment)

Next, the X-ray diagnosis apparatus 100 according to the fourth embodiment is explained. The X-ray diagnosis apparatus 100 according to the fourth embodiment stores therein in advance the correction table for every boy thickness of the subject P, selects a correction table in accordance with the body thickness estimated from the baseline frame, and corrects the target frame by use of the selected correction table.

Figure 8:
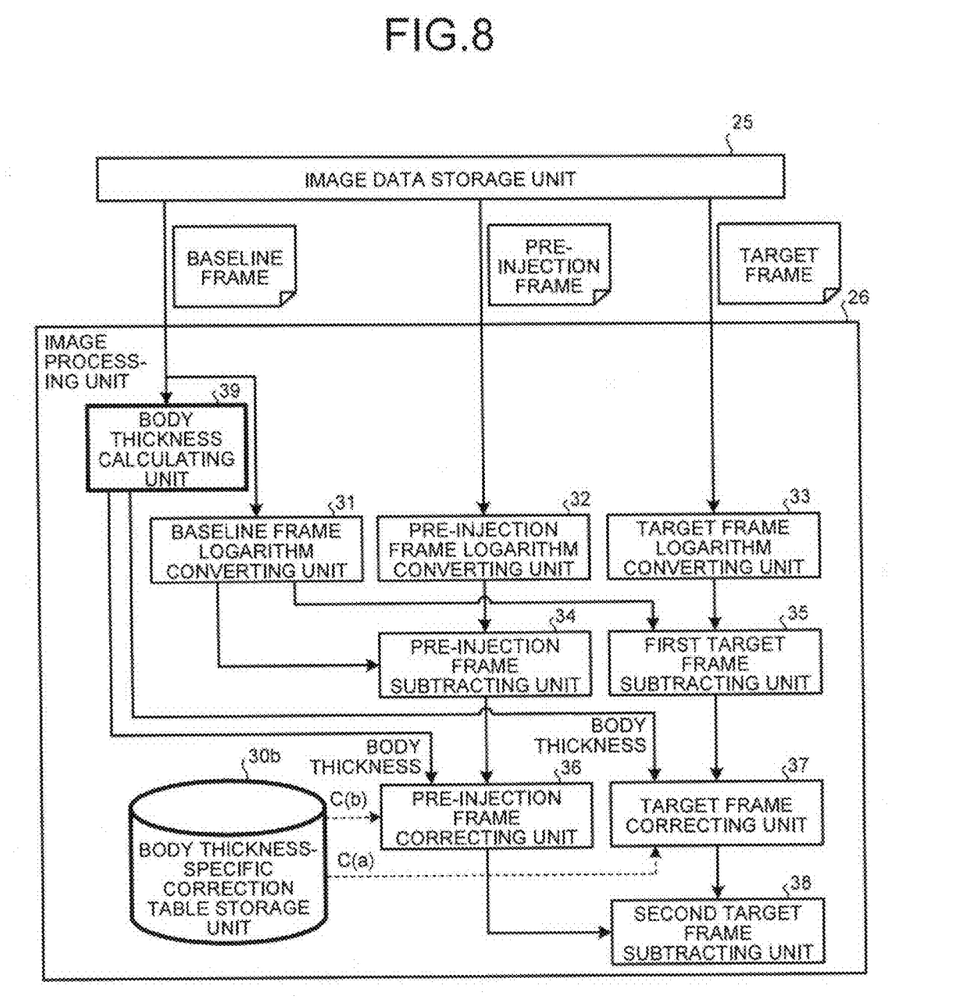
FIG. 8 is a block diagram for showing the structure of the image processing unit according to the fourth embodiment.

FIG. 8 is a block diagram for showing the structure of the image processing unit 26. As shown in FIG. 8, the image processing unit 26 according to the fourth embodiment is provided with a body thickness-specific correction table storage unit 30*b* in place of the correction table storage unit 30*a*. Moreover, the image processing unit 26 according to the fourth embodiment is further provided with a body thickness calculating unit 39.

Figure 9:
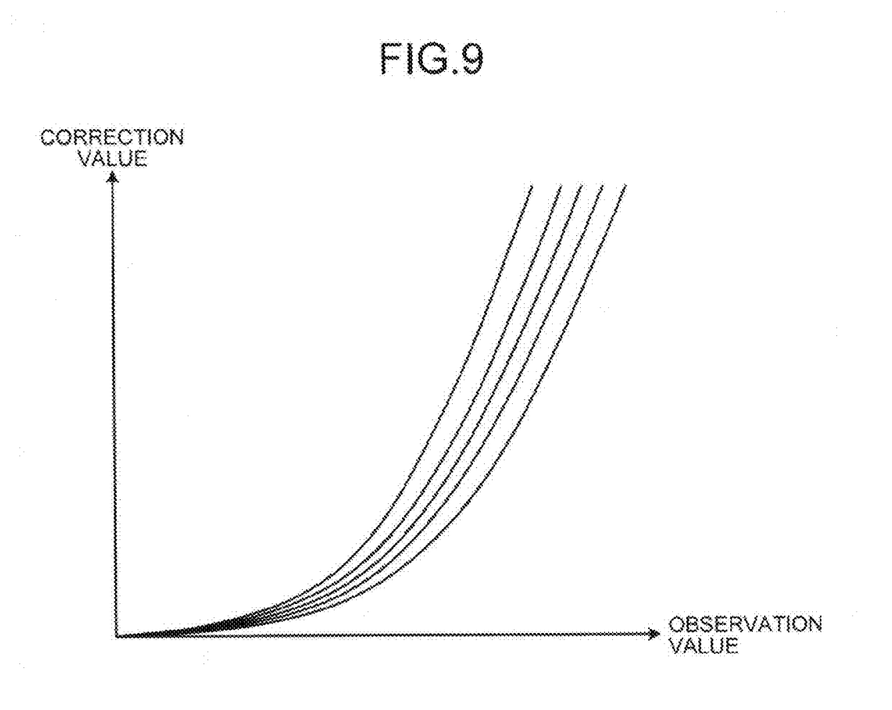
FIG. 9 is a diagram for explaining a body thickness-specific correction table storage unit according to the fourth embodiment.

The body thickness-specific correction table storage unit 30*b* stores therein, for example, a correction table for every body thickness of the subject P, as indicated in FIG. 9. FIG. 9 is a diagram for explaining the body thickness-specific correction table storage unit 30*b* according to the fourth embodiment.

The body thickness calculating unit 39 reads the "baseline frame" from the image data storage unit 25, and estimates the body thickness of the subject P based on the read-out "baseline frame". More specifically, the body thickness calculating unit 39 uses:

$$I = I_0 \exp(-\mu L)$$

and estimates the body thickness of the subject P. Here, I denotes the observation value of the X-rays, $I_0$ denotes the observation value of the X-rays when no subject P is present (when the body thickness of the subject P is "0"), μ denotes a linear absorption coefficient of a substance (water equivalent), and L denotes the body thickness. Because I, $I_0$, and μ are already known, the body thickness calculating unit 39 can estimate the body thickness L of the subject P by substituting these values into the above equation. Then, the body thickness calculating unit 39 sends the estimated body thickness of the subject P to the pre-injection frame correcting unit 36 and the target frame correcting unit 37.

When referring to the body thickness-specific correction table storage unit 30*b* uses the observation value (b) of the residual contrast material component received from the body thickness calculating unit 39, the pre-injection frame correcting unit 36 also uses the body thickness of the subject P received from the body thickness calculating unit 39. In other words, the storage in the body thickness-specific correction table storage unit 30*b* is maintained in accordance with the body thickness of the subject P, the pre-injection frame correcting unit 36 first selects a correction table in accordance with the body thickness of the subject P, and corrects the pre-injection frame by use of the correction table.

Similarly, when referring to the correction table storage unit 30 by use of the total value (a) received from the first target frame subtracting unit 35, the target frame correcting unit 37 also uses the body thickness of the subject P received from the body thickness calculating unit 39. In other words, because the storage of the body thickness-specific correction table storage unit 30*b* is maintained in accordance with the body thickness of the subject P, the target frame correcting unit 37 first selects a correction table in accordance with the body thickness of the subject P, and corrects the pre-injection frame in accordance with the selected correction table.

In this manner, according to the fourth embodiment, corrections are most suitably made in accordance with the body thickness of the subject P, and therefore the corrections can be made with still higher accuracy. In addition, according to the fourth embodiment, corrections for the "water equivalent" component do not have to be separately made. In other words, the correction curve is often affected by the "water equivalent" component. For this reason, according to the first embodiment that has been explained above, for example, it is preferable that corrections for the "water equivalent" component should be made separately from corrections for the "iodine" component. At this point, according to the fourth embodiment, corrections are made by use of a correction table that is selected in accordance with the body thickness, and therefore corrections for the "water equivalent" component do not have to be separately made, and corrections can be conducted at a time. The correction table selected in accordance with the body thickness may be combined with the first to third embodiments. In addition, an example of storing the correction table in accordance with the body thickness has been explained above, but the embodiment is not limited thereto. For example, the X-ray diagnosis apparatus 100 may store therein a correction in accordance with conditions regarding the table X-ray diagnosis apparatus or in accordance with combinations of the body thicknesses and the conditions. The conditions regarding the X-ray diagnosis apparatus may be the voltage of the X-ray tube, the source-imager distance (SID) that represents the distance between the X-ray tube and the X-ray detector, the subject-imager distance (PID) that represents the distance between the subject and the X-ray detector, the field of view (FOV) and the like or a combination thereof. These conditions may be acquired from the X-ray diagnosis apparatus 100.

(Fifth Embodiment)

Next, the fifth embodiment is explained. According to the first to fourth embodiments, the disclosed technology applied to an X-ray diagnosis apparatus has been explained, but the embodiment is not limited thereto. The disclosed technology may be applied to an image processing apparatus.

Figure 10:
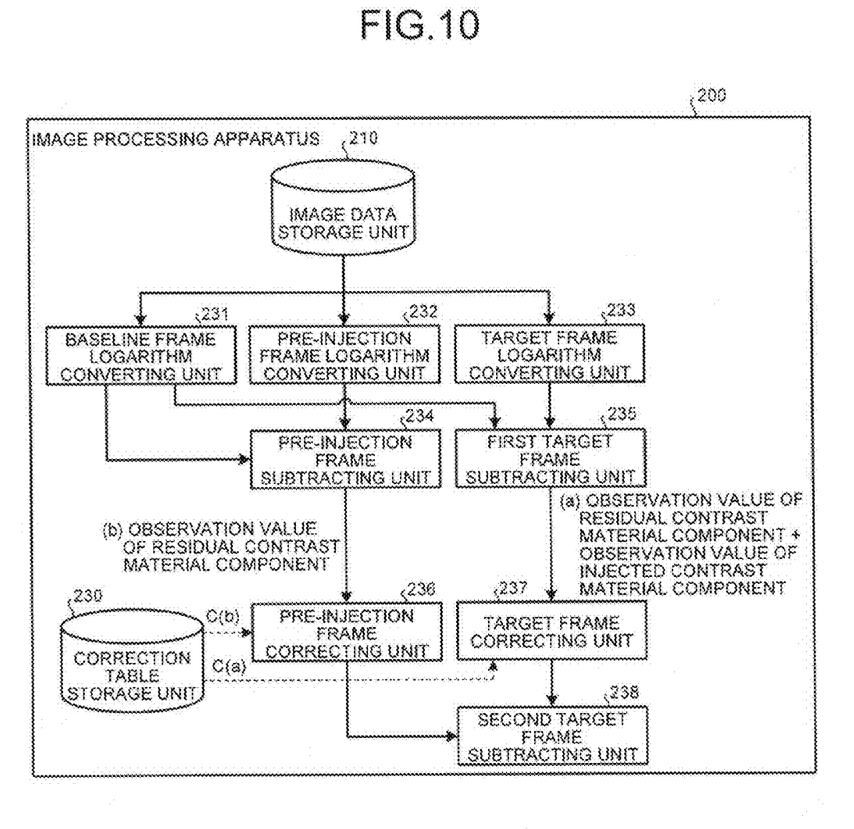
FIG. 10 is a block diagram for showing the structure of an image processing apparatus according to the fifth embodiment.

FIG. 10 is a block diagram for showing the structure of an image processing apparatus 200 according to the fifth embodiment. As indicated in FIG. 10, the image processing apparatus 200 according to the fifth embodiment includes an image data storage unit 210. The image data storage unit 210 stores therein "baseline frames", "pre-injection frames", and "target frames". The image data of these is what is acquired, for example, by the image processing apparatus 200 through the network or a recording medium from the image data acquired by the X-ray diagnosis apparatus 100.

Moreover, the image processing apparatus 200 according to the fifth embodiment includes a correction table storage unit 230. The correction table storage unit 230 has a function corresponding to that of the correction table storage unit 30a or the body thickness-specific correction table storage unit 30b according to the first to fourth embodiments.

Furthermore, the image processing apparatus 200 includes a baseline frame logarithm converting unit 231, a pre-injection frame logarithm converting unit 232, a target frame logarithm converting unit 233. The baseline frame logarithm converting unit 231 has a function corresponding to that of the baseline frame logarithm converting unit 31 according to the first to fourth embodiments. The pre-injection frame logarithm converting unit 232 has a function corresponding to that of the pre-injection frame logarithm converting unit 32 according to the first to fourth embodiments. The target frame logarithm converting unit 233 has a function corresponding to that of the target frame logarithm converting unit 33 according to the first to fourth embodiments.

Furthermore, the image processing apparatus 200 includes a pre-injection frame subtracting unit 234, and a first target frame subtracting unit 235. The pre-injection frame subtracting unit 234 has a function corresponding to that of the according to the first to fourth embodiments pre-injection frame subtracting unit 34. The first target frame subtracting unit 235 has a function corresponding to that of the according to the first to fourth embodiments first target frame subtracting unit 35.

In addition, the image processing apparatus 200 includes a pre-injection frame correcting unit 236, a target frame correcting unit 237, and a second target frame subtracting unit 238. The pre-injection frame correcting unit 236 has a function corresponding to that of the pre-injection frame correcting unit 36 according to the first to fourth embodiments. The target frame correcting unit 237 has a function corresponding to that of the target frame correcting unit 37 according to the first to fourth embodiments. The second target frame subtracting unit 238 has a function corresponding to that of the second target frame subtracting unit 38 according to the first to fourth embodiments.

(Other Embodiments)

According to the above embodiments, a "test" that includes a "treatment" has been assumed, but the embodiment is not limited thereto. The disclosed technology can be applied to a "test" that does not include "treatment. The disclosed technology may be applied to a situation of estimating, after a contrast material is injected, the concentration of a contrast material that is newly injected.

Furthermore, the disclosed technology is not always limited to the contrast material. A similar problem would arise when calculating the observation value of a certain component by performing subtraction, for example, onto images having two components or more of "substances" such as the relationship between the "water equivalent" and the "contrast material", with its correction curve being non-linear as for the "contrast material". The disclosed technology can be applied to such a case.

Figure 11:
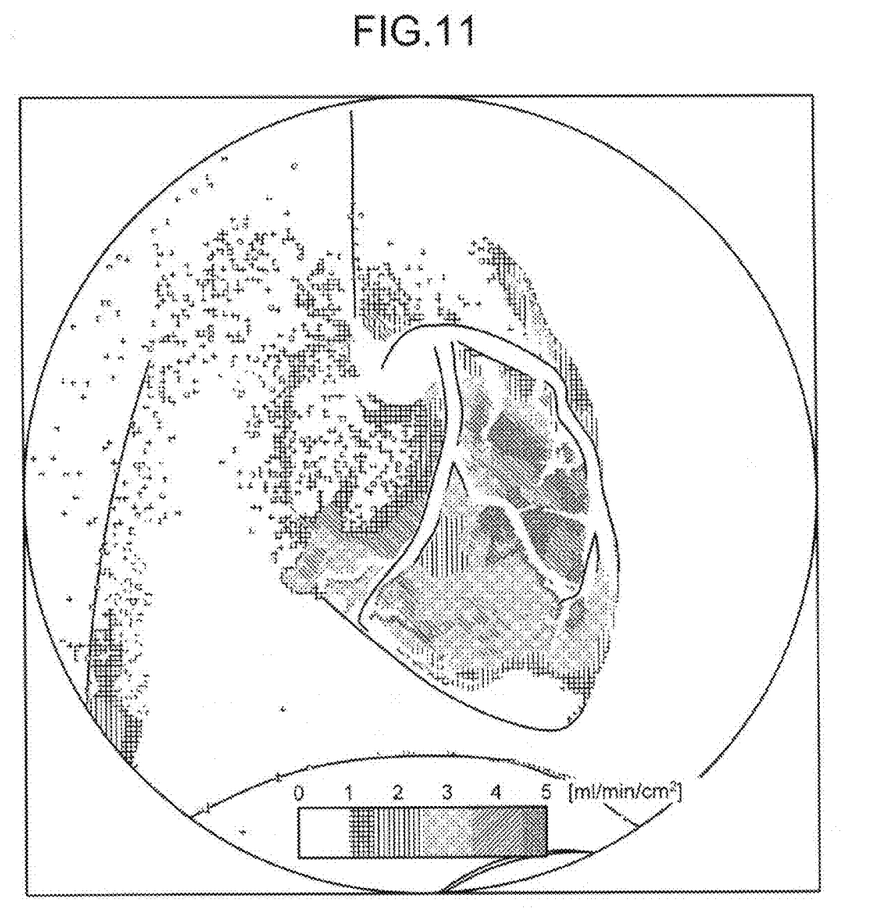
FIG. 11 is a diagram for explaining a display according to the present embodiments.

Moreover, FIG. 11 is a diagram for explaining the display according to the present embodiments. According to the present embodiments, the X-ray diagnosis apparatus 100 of the image processing apparatus 200 further includes a display controlling unit that, when displaying the analysis result based on the corrected observation value on the displaying unit, displays it together with numerical information that indicates the observation value. For example, as indicated in FIG. 11, when displaying a myocardial perfusion image as an analysis result, the X-ray diagnosis apparatus 100 or the image processing apparatus 200 displays a color scaler that indicates the numerical value of the observation value together with the myocardial perfusion image. For example, the color scaler exhibits "ml/min/cm$^2$" (the blood flow per 1 cm$^2$ that flows in for one minute), which is the unit of the concentration of contrast material and the numerical value expressed in this unit. According to the above embodiments, because the concentration of contrast material can be accurately estimated by corrections, such a color scaler may be displayed. In FIG. 11, for the simplicity of explanation, differences in colors are expressed with differences in patters.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
a correcting unit configured to identify, based on an observation value of a residual contrast material component that is injected to a subject before a predetermined timing and remains in the subject, the residual contrast material component and a new contrast material component that is newly injected to the subject after the predetermined timing regarding a contrast material component that is included in an image, and corrects an observation value of the contrast material component included in the image.

2. The image processing apparatus according to claim 1, wherein:
the image is a target image acquired after the predetermined timing and also after the new contrast material is injected in a test in which the contrast material is injected to the subject at a plurality of stages; and
the correcting unit comprises:
a residual contrast material calculating unit configured to calculate the observation value of the residual contrast material component included in the target image by subtracting an initial image acquired at an initial stage at which an accumulation amount of contrast material injected to the subject in the test is a predetermined amount or less from a pre-injection image acquired after the predetermined timing and before the new contrast material;
a total calculating unit configured to calculate a total of the observation value of the residual contrast material component and the observation value of the new contrast material component by subtracting the initial image from the target image; and
a target image correcting unit configured to correct the observation value of the new contrast material component among contrast material components included in the target image, based on a correction value corresponding to the observation value of the residual contrast material component and a correction value corresponding to the total.

3. The image processing apparatus according to claim 2, wherein the target image correcting unit stores therein in advance a correction table in which an observation value of the contrast material component and the correction value are brought into association with each other, for each body thickness of the subject, for each condition of a medical image diagnosis apparatus, or for each combination of the body thickness and the condition, and based on the corresponding correction table, correct the observation value of the new contrast material component among contrast material components included in the target image.

4. The image processing apparatus according to claim 2, wherein:
the residual contrast material calculating unit calculates the observation value of the residual contrast material component by subtracting the initial image from the pre-injection image after adjusting positions of the pre-injection image and the initial image; and
the total calculating unit calculates the total by subtracting the initial image from the target image after adjusting positions of the target image and the initial image.

5. The image processing apparatus according to claim 3, wherein:
the residual contrast material calculating unit calculates the observation value of the residual contrast material component by subtracting the initial image from the pre-injection image after adjusting positions of the pre-injection image and the initial image; and
the total calculating unit calculates the total by subtracting the initial image from the target image after adjusting positions of the target image and the initial image.

6. The image processing apparatus according to claim 1, further comprising a display controlling unit configured to display together with numerical information that indicates the observation value when displaying an analysis result of the image on a displaying unit in accordance with the observation value corrected by the correcting unit.

7. An X-ray diagnosis apparatus comprising:
an initial image acquiring unit configured to acquire an initial image of an initial stage at which an accumulation amount of contrast material injected to a subject is a predetermined amount or less in a test in which the contrast material is injected to the subject at a plurality of stages;
a pre-injection image acquiring unit configured to acquire a pre-injection image after a predetermined timing and before a new contrast material is injected;
a target image acquiring unit configured to acquire a target image after the predetermined timing and also after the new contrast material is injected; and
a correcting unit configured to correct the observation value of a contrast material component newly injected after the predetermined timing based on an observation value of a residual contrast material component included in the target image, among the contrast material components included in the target image, wherein:
the correcting unit comprises:
a residual contrast material calculating unit configured to, by subtracting the initial image from the pre-injection image, calculate an observation value of the residual contrast material component;
a total calculating unit configured to, by subtracting the initial image from the target image, calculate a total of the observation value of the residual contrast material component and an observation value of a contrast material component newly injected after the predetermined timing; and
a target image correcting unit configured to, based on a correction value corresponding to the observation value of the residual contrast material component and a correction value corresponding to the total, correct the observation value of a contrast material component newly injected after the predetermined timing among contrast material components included in the target image.

8. The X-ray diagnosis apparatus according to claim 7, further comprising a storage unit that stores therein an acquisition condition for acquiring the initial image, wherein:
the pre-injection image acquiring unit and the target image acquiring unit acquires the pre-injection image and the target image in accordance with the acquisition condition by referring to the storage unit.

9. The X-ray diagnosis apparatus according to claim 7, further comprising a display controlling unit configured to when displaying an analysis result of the target image based on the observation value corrected by the correcting unit, displays it together with numerical information indicating the observation value.

* * * * *